(12) United States Patent
Hamid et al.

(10) Patent No.: US 12,105,077 B2
(45) Date of Patent: Oct. 1, 2024

(54) ASSESSING CHARACTERISTICS OF SUBTERRANEAN FORMATIONS USING MICRO-COMPUTED TOMOGRAPHY AND ROCK MECHANICS TESTING

(71) Applicant: Saudi Arabian Oil Company, Dhahran (SA)

(72) Inventors: Osman Hamid, Dhahran (SA); Hamza M. Aljamaan, Dammam (SA); Mohammad H. Altwaijri, Dhahran (SA); Ivan Deshenenkov, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 321 days.

(21) Appl. No.: 17/652,551

(22) Filed: Feb. 25, 2022

(65) Prior Publication Data

US 2023/0273175 A1     Aug. 31, 2023

(51) Int. Cl.
G01N 23/046    (2018.01)
G01N 24/08     (2006.01)
G01N 33/24     (2006.01)

(52) U.S. Cl.
CPC ......... *G01N 33/241* (2013.01); *G01N 23/046* (2013.01); *G01N 24/081* (2013.01); *G01N 2223/419* (2013.01); *G01N 2223/616* (2013.01)

(58) Field of Classification Search
CPC .. G01N 23/046; G01N 24/081; G01N 33/241; G01N 2223/419; G01N 2223/616
See application file for complete search history.

(56) References Cited

U.S. PATENT DOCUMENTS

| | | | |
|---|---|---|---|
| 9,507,047 B1 * | 11/2016 | Dvorkin | G01V 5/101 |
| 9,920,233 B2 | 3/2018 | Husein et al. | |
| 10,000,690 B2 | 6/2018 | Wu et al. | |
| 10,725,012 B2 | 7/2020 | Lander et al. | |

(Continued)

OTHER PUBLICATIONS

Liu et al., "In situ deformation analysis of a fracture in coal under cyclic loading and unloading," Energies, Oct. 2021, 14(20):6474, 16 pages.

(Continued)

*Primary Examiner* — Eric S. McCall
(74) *Attorney, Agent, or Firm* — Fish & Richardson P.C.

(57) ABSTRACT

A computer system obtains a first set of micro-computed tomography (micro-CT) data representing a rock sample obtained from a subterranean formation that includes gas-bearing sandstone. The system obtains a plurality of second sets of micro-CT data in a sequence, each representing the rock sample after a performance of a corresponding triaxial shear test on the rock sample. Performing each triaxial shear test includes applying a triaxial load force to the rock sample, and removing the triaxial load force from the rock sample. The system estimates, based on the first micro-CT data and the plurality of second sets of micro-CT data, one or more characteristics of the underground formation, including a permeability of the underground formation and/or a porosity of the underground formation. The system causes one or more resource extraction operations to be performed on the underground formation based on the one or more characteristics of the underground formation.

13 Claims, 14 Drawing Sheets

(56) References Cited

U.S. PATENT DOCUMENTS

2017/0299485 A1* 10/2017 Lai ........................... G01N 3/08
2017/0299486 A1* 10/2017 Han ....................... G01N 33/24
2019/0369282 A1* 12/2019 Liu ........................ G01V 1/284

OTHER PUBLICATIONS

Voorn et al., "Porosity, permeability and 3D fracture network characterisation of dolomite reservoir rock samples," Journal of Petroleum Science and Engineering, Mar. 2015, 127:270-285, 39 pages.

* cited by examiner

ASSESSING CHARACTERISTICS OF SUBTERRANEAN FORMATIONS USING MICRO-COMPUTED TOMOGRAPHY AND ROCK MECHANICS TESTING

TECHNICAL FIELD

The disclosure relates to systems and methods for assessing characteristics of subterranean formations using micro-computed tomography and rock mechanics testing.

BACKGROUND

A well is used to bring natural resources, such as oil or natural gas, from a subterranean formation to the surface of the earth. A well can be created and utilized according to several stages, including a drilling stage, a completion stage, and a production stage.

During the drilling stage, a wellbore is formed by drilling a hole through the surface of the earth and through a portion of the subterranean formation, such that the contents of the subterranean formation can be accessed. Further, the wellbore can be reinforced, for example, by installing a casing or pipe along its length.

During the completion stage, the well is made ready for production or injection. For example, the bottom of the wellbore can be prepared to particular specifications. As another example, production tubing and other downhole tools can be installed in or around the wellbore to facilitate the extraction of natural resources from the well.

During the production stage, natural resources are extracted from the subterranean formation and brought to the surface of the earth. For example, oil or natural gas contained within the subterranean formation can be brought to the surface of the earth, such that they can be processed and used as sources of energy or used as a part of other industrial applications.

SUMMARY

In general, during the operation of a well, a subterranean formation may be subjected to repeated loading and unloading forces. For example, portions of the subterranean formation may be subjected to loading forces during an injection process. As another example, portions of the subterranean formation may be subjected to unloading forces during a depletion process.

Repeated loading and unloading forces can lead to increases and decreases in the effective stress in the poroelastic media of the subterranean formation, respectively, and can result in changes in the characteristic of the subterranean formation over time. For example, these forces can result in changes in the permeability and/or porosity of the subterranean formation and can change the manner in which fluids flow through the subterranean formation.

This disclosure describes systems and techniques for assessing the characteristics of a subterranean formation using micro-computing tomography (micro-CT) and rock mechanics testing. In an example implementation, a sample of a subterranean formation is imaged using a micro-CT scanner to determine the characteristics of the pores and pore throats in the sample. Further, the sample is repeatedly subjected to loading and unloading forces in a sequence. For example, several non-destructive triaxial shear tests can be performed on the sample in a sequence. During each triaxial shear test, a triaxial load force can be applied to the sample for a period of time and subsequently removed from the sample. Further, the sample can be imaged using the micro-CT scanner to determine the changes to the pores and pore throats of the sample with each successive test. Based on the imaging data, a rock analysis system can determine one or more characteristics of the subterranean formation, including the permeability and the porosity of the rock formation over time.

Further still, the operations of a well can be controlled based on the determined characteristics of the subterranean formation. For example, the well can be operated such that the subterranean formation remains in an elastic regime during repeated injection and/or depletion processes (for example, such that the subterranean formation is less likely to fracture during operations). Accordingly, the well can be operated in a safer, more reliable, and more efficient manner.

In an aspect, a method includes: obtaining, by a computer system, a first set of micro-computed tomography (micro-CT) data representing a rock sample, where the rock sample is obtained from a subterranean formation including gas-bearing sandstone; obtaining by the computer system, a plurality of second sets of micro-CT data in a sequence, where each of the second sets of micro-CT data represents the rock sample after a performance of a corresponding triaxial shear test on the rock sample, and wherein performing each triaxial shear test includes: applying a triaxial load force to the rock sample, and removing the triaxial load force from the rock sample; estimating, by the computer system based on the first micro-CT data and the plurality of second sets of micro-CT data, one or more characteristics of the underground formation, where the one or more characteristics includes at least one of: a permeability of the underground formation, or a porosity of the underground formation; and causing, by the computer system, one or more resource extraction operations on the underground formation based on the one or more characteristics of the underground formation.

Implementations of this aspect can include one or more of the following features.

In some implementations, the rock sample can include a cylindrical portion of rock extending along an axis, and an aperture defined through the cylindrical portion and extending along the axis.

In some implementations, a diameter of the cylindrical portion can be approximately 3 inches in height and can have an outer diameter of approximately 1.5 inches. Further, the aperture can have a diameter of approximately 0.5 inches.

In some implementations, each of the first micro-CT data and the plurality of second sets of micro-CT data can include one or more images having a voxel size of 3 μm or less along a dimension.

In some implementations, estimating the one or more characteristics of the underground formation can include modeling a fluid of flow through the underground formation.

In some implementations, estimating the one or more characteristics of the underground formation can include modeling an elasticity of the underground formation.

In some implementations, estimating the one or more characteristics of the underground formation can include determining a change in a pore size of the underground formation in response to performance of the triaxial shear tests.

In some implementations, estimating the one or more characteristics of the underground formation can include determining a change in a pore throat size of the underground formation in response to performance of the triaxial shear tests.

In some implementations, estimating the one or more characteristics of the underground formation can include determining a change in an acoustic velocity through the underground formation.

In some implementations, the one or more resource extraction operations can include regulating an extraction of resources from the underground formation based on the one or more characteristics of the underground formation.

In some implementations, the one or more resource extraction operations can include regulating an injection of a substance into the underground formation based on the one or more characteristics of the underground formation.

Other implementations are directed to systems, devices, and devices for performing some or all of the methods. Other implementations are directed to one or more non-transitory computer-readable media, including one or more sequences of instructions which, when executed by one or more processors, causes the performance of some or all of the methods.

The details of one or more embodiments are set forth in the accompanying drawings and the description. Other features and advantages will be apparent from the description and drawings and from the claims.

DETAILED DESCRIPTION

In general, during the operation of a well, a subterranean formation may be subjected to repeated loading and unloading forces. For example, during an injection process, material (for example, water) may be introduced into a subterranean formation to increase or maintain a fluid pressure within subterranean formation and/or to drive resources towards a well. Introduction of the material into the subterranean formation may subject the subterranean formation to loading forces. As another example, during a depletion process, material (for example, subterranean resources, such as oil, gas, etc.) may be removed from the subterranean formation. Removing the material from the subterranean formation may subject the subterranean formation to unloading forces.

Repeated loading and unloading forces can lead to increases and decreases, respectively, in the effective stress in the poroelastic media of the subterranean formation, and can result in changes in the characteristic of the subterranean formation over time. For example, these forces can result in changes in the permeability and/or porosity of the subterranean formation and can change the manner in which fluids flow through the subterranean formation.

This disclosure describes systems and techniques for assessing the characteristics of a subterranean formation using micro-computing tomography (micro-CT) and rock mechanics testing.

In an example implementations, a sample of a subterranean formation (for example, a "thick wall cylinder" rock sample) is imaged using a micro-CT scanner to determine the characteristics of the pores and pore throats in the sample. Further, the sample is repeatedly subjected to loading and unloading forces in a sequence. For example, several triaxial shear tests can be performed on the sample in a sequence. During each triaxial shear test, a triaxial load force can be applied to the sample for a period of time and subsequently removed from the sample. Further, the sample can be imaged using the micro-CT scanner to determine the changes to the pores and pore throats of the sample with each successive test. Based on the imaging data, a rock analysis system can determine one or more characteristics of the subterranean formation, including the permeability and the porosity of the rock formation over time.

Further still, the operations of a well can be controlled based on the determined characteristics of the subterranean formation. For example, the well can be operated such that the subterranean formation remains in an elastic regime during repeated injection and/or depletion processes. Accordingly, the subterranean formation is less likely to fracture during operations (for example, compared to operations that do not include the performance of these rock assessment techniques). Thus, the well can be operated in a safer, more reliable, and more efficient manner.

Figure 1A:
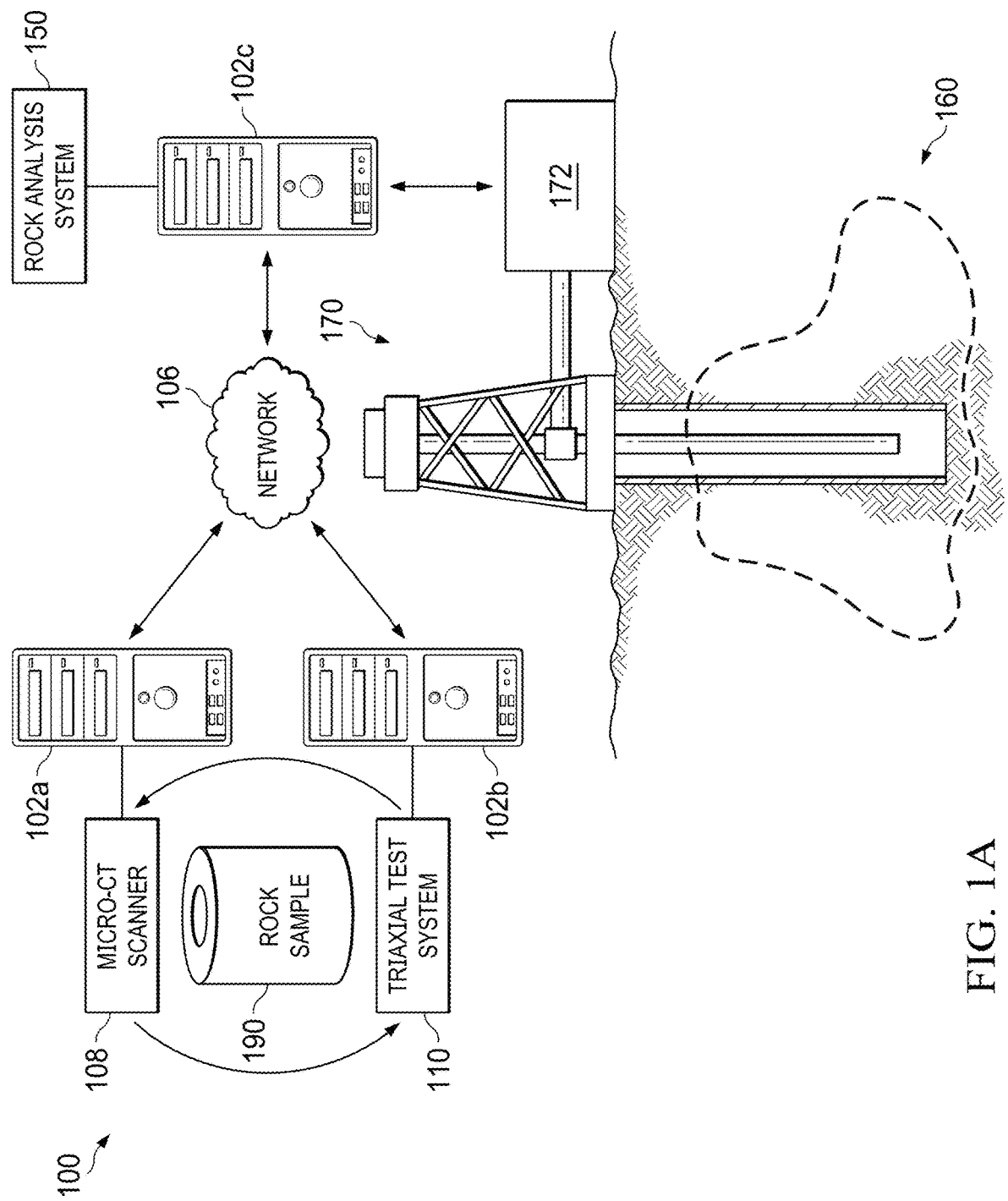
FIG. 1A is a diagram of an example system for assessing the characteristics of a subterranean formation.

FIG. 1A shows an example system 100 for assessing the characteristics of a subterranean formation 160 and controlling the operations of a well 170. The system 100 includes several computer systems 102a-102c communicatively coupled to one another through a network 106. The system also includes a micro-CT scanner 108 configured to generate imaging data of a rock sample 190 (for example, one or more sets of micro-CT images of the rock sample 190). Further, the system also includes a triaxial test system 110 configured to perform triaxial shear tests on the rock samples 190. Further, a rock analysis system 150 is maintained on at least one of the computer systems (for example, the computer system 102c).

During an example operation of the system 100, a rock sample 190 is obtained from the subterranean formation 160. In some implementations, the subterranean formation 160 can include sandstone bearing one or more types of hydrocarbon gases. Example hydrocarbon gases include methane ($CH_4$), ethane ($C_2H_6$), propane ($C_3H_8$), butanes ($C_4H_{10}$), pentanes ($C_5H_{12}$), hexane ($C_6H_{14}$), and heptane ($C_7H_{16}$), among others.

Figure 1B:
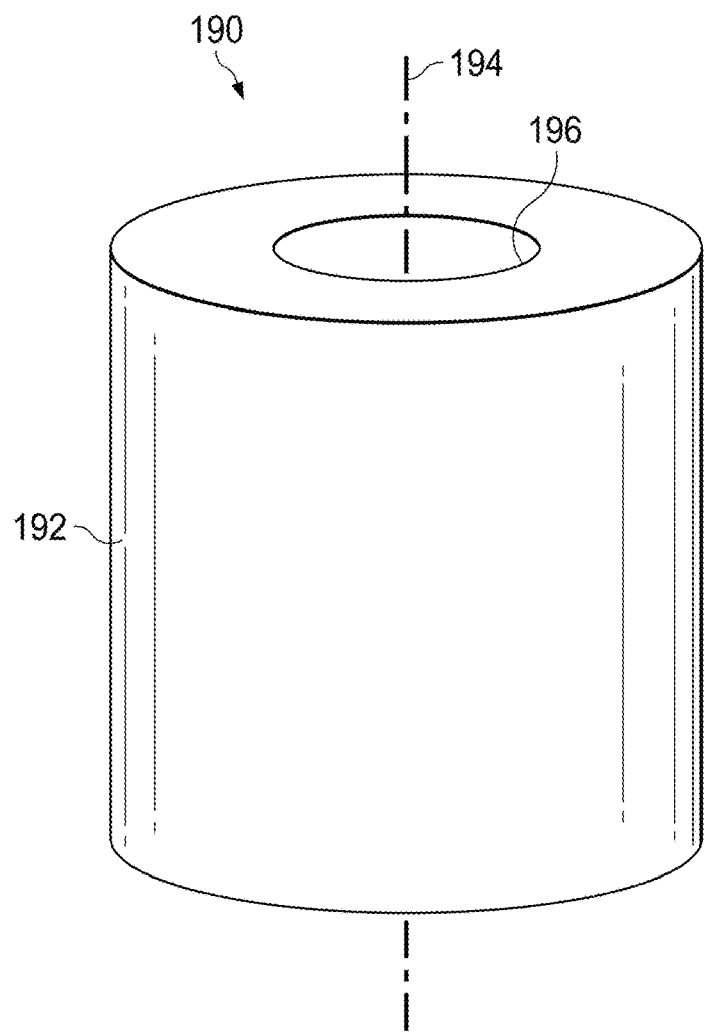
FIG. 1B is a diagram of an example thick wall cylinder (TWC) rock sample.

In some implementations, the rock sample 190 can be a "thick wall cylinder" sample of rock from the subterranean formation 160. For example, as shown in FIG. 1B, the rock sample 190 can include a cylindrical portion 192 of rock extending along an axis 194. Further, the rock sample 190 can include an aperture 196 defined through the cylindrical portion 192 and extending along the axis 194. In some implementations, the cylindrical portion 192 can be approximately 3 inches in height (for example, 3 inches±10%), and can have an outer diameter of approximately 1.5 inches (for example, 1.5 inches±10%). Further, the aperture 196 can have a diameter of approximately 0.5 inches (for example, 0.5 inches±10%).

The micro-CT scanner 108 obtains imaging data regarding the rock sample 190, and provides the imaging data to the computer system 102a. As an example, the micro-CT scanner 108 can obtain a set of one or more micro-CT images, each image representing a particular cross-section or "slab" of the rock sample 190. In some implementations, at least some of the micro-CT images can have pixels or voxels having 3 μm or less along a dimension. For example, at least some of the micro-CT images can be two-dimensional images, with a pixel size of 3 μm×3 μm or smaller. As another example, at least some of the micro-CT images can be three-dimensional images, with a voxel size of 3 μm×3 μm×3 μm or smaller.

In some implementations, the micro-CT images can represent the characteristics of one or more pores or pore throats in the rock sample 190. For example, the micro-CT images can show the shape, dimensions, and distribution of pores and/or pore throats in the rock sample 190. In general, a pore can refer to a discrete void within a rock, which can contain air, water, hydrocarbons, or other fluids. Further, a pore throat can refer to a pore space at the point where two grains of rock meet, which connects two larger pore volumes.

Subsequently, multiple triaxial shear tests are performed on the rock sample 190 in a sequence using the triaxial test system 110. In some implementations, the triaxial test system 110 can be controlled using the computer system 102b.

During each triaxial shear test, a trial load force is applied to the rock sample 190 for a period of time, after which the load force is removed from the rock sample 190. This may be referred to as "loading" and "unloading" the rock sample 190.

In general, a triaxial shear test refers to a technique in which stresses or forces are applied to a sample (for example, the rock sample 190) in a way that results in stresses along one axis being different from the stresses in perpendicular directions. This can be achieved by placing the sample between two parallel platens that apply stress in one direction (for example, a vertical direction), and applying fluid pressure to the sample to apply stress in the perpendicular directions (for example, horizontal directions).

The application of different compressive stresses in the test apparatus can cause shear stress to develop in the rock sample 190. Further, the loads can be increased and deflections monitored until failure of the rock sample 190. For example, during the test, the surrounding fluid can be pressurized. The stress on the platens can be increased until the material in the cylinder fails and forms sliding regions within itself, known as shear bands. In some implementations, the geometry of the shearing in a triaxial test may cause the rock sample 190 to become shorter while bulging out along the sides. The stress on the platen is then reduced, and the water pressure pushes the sides back in, causing the rock sample 190 to grow taller again. In some implementations, this loading and unloading cycle can be repeated several times while collecting stress and strain data about the sample.

After the performance of each triaxial shear test, the micro-CT scanner 108 obtains additional imaging data regarding the rock sample 190, and provides the imaging data to the computer system 102a. As an example, the micro-CT scanner 108 can obtain additional sets of micro-CT images, each image representing a particular cross-section or "slab" of the rock sample 190. Further, these micro-CT images can represent the changes to the structure of the rock sample 190 over time, as the rock sample 190 experiences each cycle of loading and unloading forces.

For instance, the rock sample 190 can be initially imaged using the micro-CT scanner 108, prior to the application of any loading or unloading forces. Subsequently, the rock sample 190 can be subjected to one or more cycles of loading and unloading forces, then imaged an additional time using the micro-CT scanner 108 after the performance of each cycle.

In some implementations, the rock sample 190 can be subjected to at least ten cycles of loading and unloading forces. Further, the rock sample 190 can be imaged at least one time prior to the application of any loading or unloading and at least one time subsequent to the performance of each cycle of loading and unloading forces (for example, at least ten additional times).

In some implementations, the micro-CT images can represent changes to the characteristics of one or more pores or pore throats in the rock sample 190. For example, the micro-CT images can show changes to the shape, dimensions, and distribution of pores and/or pore throats in the rock sample 190 (for example, due to the loading and unloading forces).

The rock analysis system 150 receives the sets of micro-CT images from the micro-CT scanner 108 and the computer system 102a. Further, the rock analysis system 150 determines one or more characteristics of the subterranean formation 160 based on the micro-CT images. In at least some implementations, the rock analysis system 150 can determine the permeability and/or porosity of the subterranean formation 160. In general, permeability refers to a measure of the ability of a porous material to allow fluids to pass through it. Permeability can be expressed, for example, in units of $m^2$ or Darcy (d). In general, porosity refers to a measure of the void spaces in a material and is a fraction of the volume of voids over the total volume. In at least some implementations, the rock analysis system 150 can model fluid flow through the subterranean formation 160. Example techniques for determining characteristics of the subterranean formation 160 are described in future detail below.

Further, the data generated by the rock analysis system 150 can be used to control the operation of the well 170. For example, the data generated by the rock analysis system 150 can be used to model an elasticity of the subterranean formation 160 in response to repeated loading and unloading forces, such as those that might be experienced during injection and depletion processes. Further, the operations of the well 170 can be controlled, such that the subterranean formation 160 remains in an elastic regime during repeated injection and/or depletion processes (for example, such that the subterranean formation is less likely to fail during operations). Accordingly, the well 170 can be operated in a safer, more reliable, and more efficient manner.

In some implementations, the rock analysis system 150 can automatically control the operation of the well 170. For example, the rock analysis system 150 can be communicatively coupled to a control system 172 of the well 170, and transmit commands to the control system 172 for execution. In some implementations, the commands can include one or more operational parameters regarding an injection or depletion process.

In some implementations, the rock analysis system 150 can provide data to a human operator to assist in the operation of the well 170. For example, the rock analysis system 150 can provide continuous feedback to the operation regarding the characteristics of the subterranean formation 160, such that the operator is kept apprised of the condition of the subterranean formation 160 during operation of the well 170. Further, the rock analysis system 150 can indicate one or more suggested commands to the operation for manual execution. For example, the commands can include one or more suggested operational parameters regarding an injection or depletion process.

In general, each of the computer systems 102a-102c can include any number of electronic devices that are configured to receive, process, and transmit data. Examples of the computer systems 102a-102c include client computing devices (such as desktop computers or notebook computers), server computing devices (such as server computers or cloud computing systems), mobile computing devices (such as cellular phones, smartphones, tablets, personal data assistants, notebook computers with the networking capability), wearable computing devices (such as a smartphone or a headset), and other computing devices capable of receiving, processing, and transmitting data. In some implementations, the computer systems 102a-102c can include computing devices that operate using one or more operating systems (as examples, Microsoft Windows, Apple macOS, Linux, Unix, Google Android, and Apple iOS, among others) and one or more architectures (as examples, x86, PowerPC, and ARM, among others). In some implementations, one or more of the computer systems 102a-102c need not be located locally with respect to the rest of the system 100, and one or more of the computer systems 102a-102c can be located in one or more remote physical locations.

Each the computer systems 102a-102c can include a respective user interface that enables users to interact with the computer system 102a-102c and the rock analysis system 150, such as to view data from one or more of the computer systems 102a-102c or the rock analysis system 150, transmit data from one computer system 102a-102c to another, or to issue commands to one or more of the computer systems 102a-102c or the rock analysis system 150. Commands can include, for example, any user instruction to one or more of the computer system 102a-102c or the rock analysis system 150 to perform particular operations or tasks. In some implementations, a user can install a software application onto one or more of the computer systems 102a-102c to facilitate the performance of these tasks.

In FIG. 1A, the computer systems 102a-102c are illustrated as respective single components. However, in practice, the computer systems 102a-102c can be implemented on one or more computing devices (for example, each computing device including at least one processor such as a microprocessor or microcontroller). As an example, the computer system 102c can be a single computing device that is connected to the network 106, and the rock analysis system 150 can be maintained and operated on a single computing device. As another example, the computer system 102c can include multiple computing devices that are connected to the network 106, and the rock analysis system 150 can be maintained and operated on some or all of the computing devices. For instance, the computer system 102c can include several computing devices, and the rock analysis system 150 can be distributed on one or more of these computing devices.

The network 106 can be any communications network through which data can be transferred and shared. For example, the network 106 can be a local area network (LAN) or a wide-area network (WAN), such as the Internet. The network 106 can be implemented using various networking interfaces, for instance wireless networking interfaces (such as Wi-Fi, Bluetooth, or infrared) or wired networking interfaces (such as Ethernet or serial connection). The network 106 also can include combinations of more than one network and can be implemented using one or more networking interfaces.

Example Rock Analysis Techniques

As described above, various techniques can be used to analyze the characteristics of a rock sample, and correspondingly, the characteristics of a subterranean formation from which the rock sample was obtained.

For example, a rock sample (for example, a thick wall cylinder) can be imaged at a time $T_1$ using a micro-CT scanner to map the pore space and pore throats of the rock sample. Further, the rock sample can be subjected to loading and unloading forces using different axial and confining pressures. Subsequently, the rock samples can be further imaged using the micro-CT scanner at a time $T_2$ to map changes to pore space and pore throats of the rock sample. This process can be repeated over multiple cycles (for example, ten or more cycles of loading, unloading, and imaging). Further, the imaging data can be interpreted and extrapolated to match a number of injection and depletion scenarios, and the fluid flow can be numerically simulated at pore scale using direct flow modeling within the pore space with the Navier-Stokes-Brinkman equation to evaluate changes in permeability and porosity.

In some implementations, performance of these techniques can be used to establish injection and depletion guidelines for operating a well. Further, these techniques can be used for oil recovery to ensure safe operations within an elastic limit to avoid or otherwise reduce the occurrence of permeability damage and can lead to the safe, effective, and efficient operation of a well.

For instance, the elastic and plastic behavior of a reservoir rock can be characterized, and the resulting information can be used to develop a series of guidelines for managing a reservoir. As an example, these techniques can be used to manage a sandstone reservoir, which is characterized by a network of pores that are interconnected to one another via pore throats. During gas storage cyclicity, the reservoir rock can be subjected to loading during injection and unloading during depletion, which can lead to increases and decreases of the effective stresses in the poroelastic media of the reservoir. Accordingly, guidelines for reservoir development can be developed to operate a field within the elastic limit of the formation to ensure that the permeability of the formation is not impaired and such that fluid can continuously flow in and out of the reservoir.

In particular, reservoir deformation can be induced by a compressive failure mode due to loading and unloading during multiple sequences of injection and depletion. This process may lead to compaction of the reservoirs, which can produce adverse effects such as a reduction in porosity and permeability, pore-volume collapse, solids production, and wellbore deformation or failure. At least some of these effects can be studied using core plugs testing and micro-CT images. Further, at least some of these effects can be verified with finite element modeling, log measurements from wellbores drilled after production, and pressure transient analysis.

Based on these factors, there is a need to accurately measure the dynamic permeability and porosity by characterizing the pore space and pore throat collapse for the current and future injection and depletion operations.

In general, compressive failure is one of the main failure modes in continuum damage mechanics that leads to pore size collapse and pore throat damage. These effects may be randomly distributed, depending on the initial pore size and pore throat (for example, initial permeability and porosity), the magnitude of applied loading and unloading forces, the degree of cementation between grains, the mechanical properties of the formation (for example, Young's modulus and Poisson's ratio), the degree of saturation, and the grain size distribution. This compressive failure can occur through the organization of the microstructure and the grains, leading to localization failure.

Figure 2:
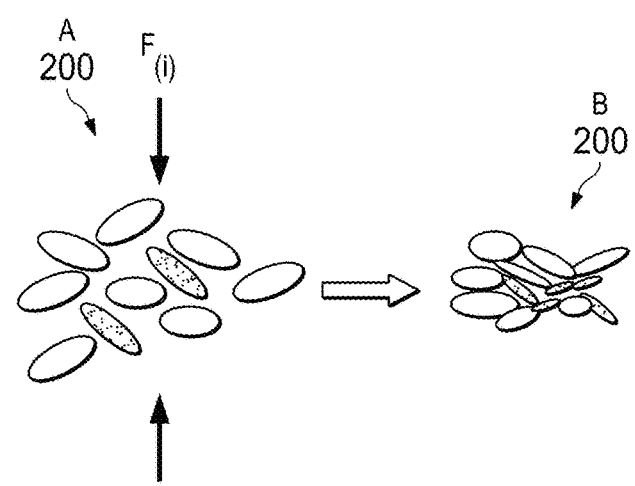
FIG. 2 is a diagram of an example pore size distribution of pores before applying forces and pore size reduction and reorganization of the pores due to mechanical damage by the acting forces.

FIG. 2 is an example of the pore size distribution of pores 200 before applying forces (A) and pore size reduction and reorganization of the pores 200 due to mechanical damage by the acting forces (B). These changes in porosity can be due to a reduction in pore size or pore throat disconnection and can lead to permeability damage and fluid flow restriction in the formation.

Figure 3:
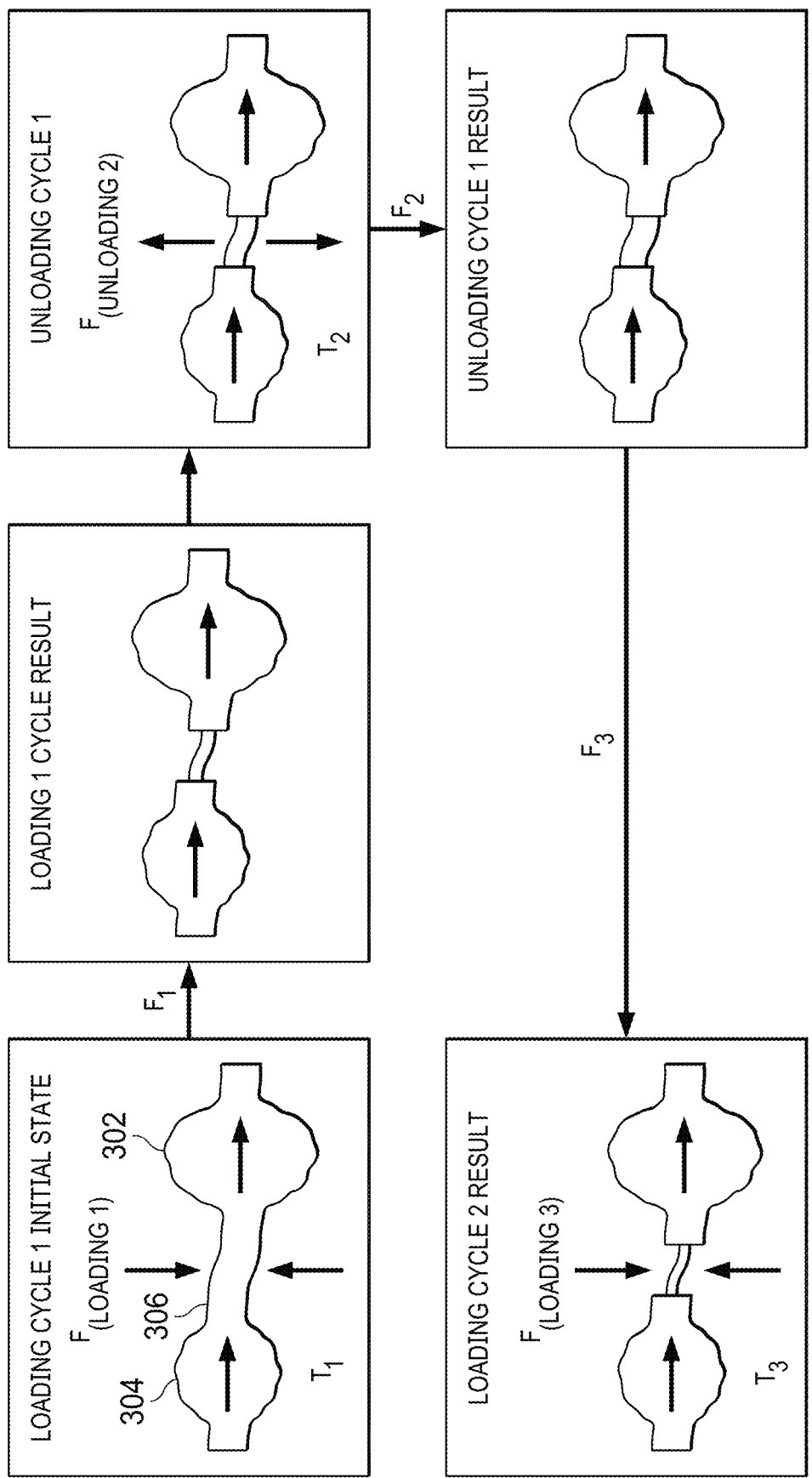
FIG. 3 shows an example of pore throat characterization during loading and unloading processes.

FIG. 3 shows an example of the pore throat characterization during loading and unloading processes. In this example, a simplified representation of a sample includes two pores 302 and 304 that are interconnected by a pore throat 306 extending between them. When a loading force $F_1$ is applied to the sample at a time $T_1$, this may cause the pore throat 306 to narrow, resulting in a narrowing the fluid pathway between the pores 302 and 304. If the narrowing of the pore throat 306 is within the plastic limits of the sample, the narrowing can be reversed (for example, when the loading force is removed from the sample).

However, if the narrowing of the pore throat 306 exceeds the plastic limits of the sample, the narrowing may be irreversible. For example, if the sample is subsequently subjected to an unloading force $F_2$ at a time $T_2$, the narrowing of the pore throat 306 may remain, resulting in permanent damage to the pore throat 306. This damage may be exacerbated by further loading and unloading cycles on the sample.

In general, a reservoir formation responds to the loading and unloading through changes in the magnitude of the effective stresses due to changes in the formation pressure. The loading and unloading forces may be partially supported by the rock matrix and partially supported by the pressurized fluid within the rock pore space. When fluid pressure is reduced, a greater portion of the load is transferred to the rock matrix, which leads to deformation of the formation, changes to the pore size, and pore throat damage. In contrast, fluid injection operations can lead to a decrease in the effective stress, resulting in stress relief. In some cases, stress relief may result in a pore system regaining some of its original shapes (for example, if the deformation was within the elastic limits of the formation). However, in some implementations, the pore system may be permanently damaged (for example, if the deformation exceeds the elastic limits of the formation, and enters into the plastic deformation regime).

One of the main drivers of formation compaction is the effective stress $\sigma'_{ij}$, which is based on the relationship between total stress $\sigma_{ij}^T$ and formation pressure ($P_o$). The effective stress ($\sigma'_{ij}$) can be expressed as:

$$\sigma'_{ij} = \sigma_{ij}^T - \alpha P_o \delta_{ij} \qquad \text{Eq. 1.}$$

α is Biot's coefficient, for soft sediment, it was found to be close to one.

$\delta_{ij}$ is the Kronecker delta, which equals one if i=j and equals zero otherwise.

$\sigma'_v$ is the effective vertical stress magnitude, mainly controlling the compaction processes.

$\delta'_{Hmin}$ is the effective minimum horizontal stress, mainly impacting permeability changes.

Example testing results are described below.

Example Testing Results

Figure 4:
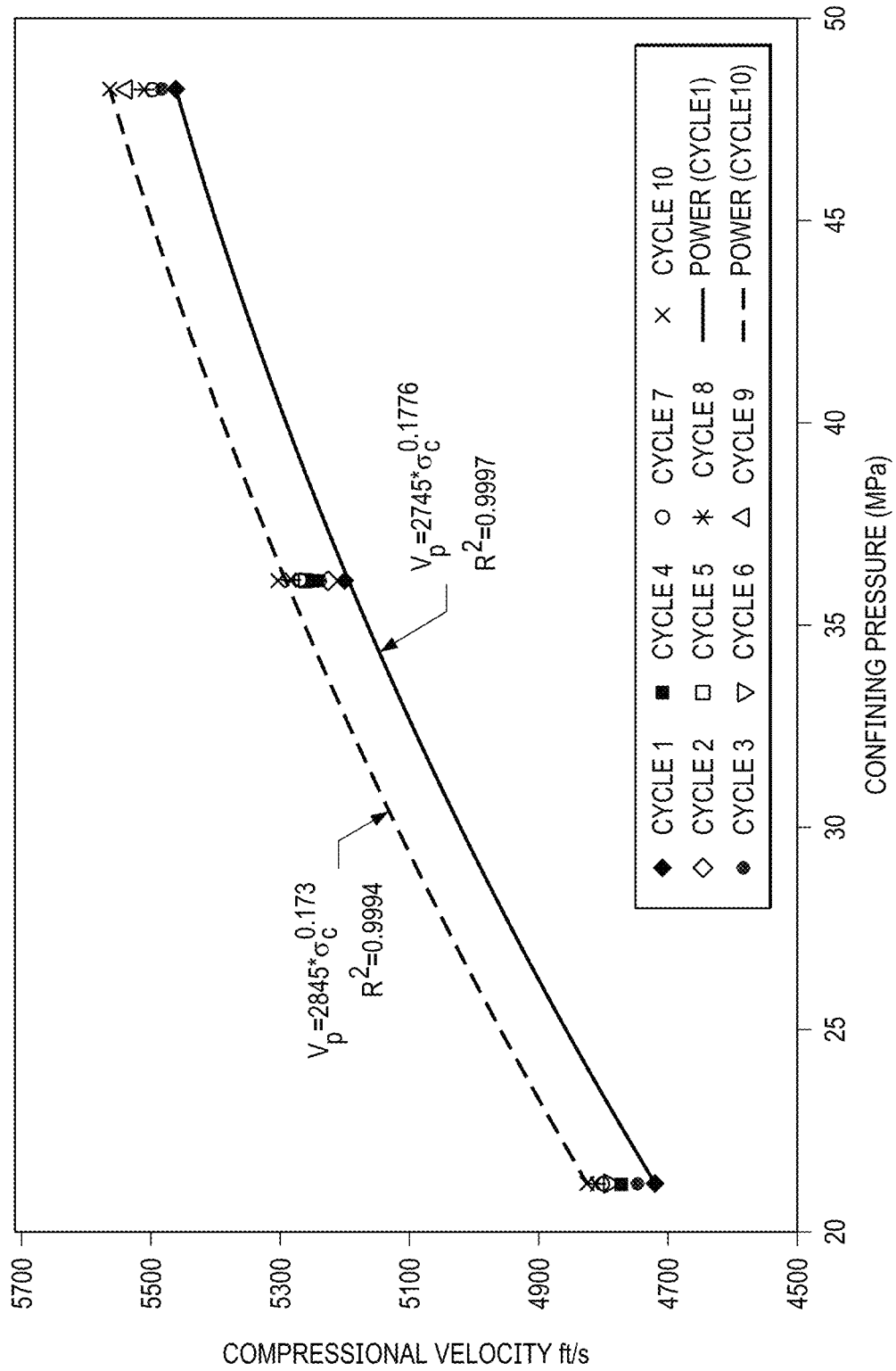
FIG. 4 is a plot showing a series of compressional velocities measurements under triaxial testing conditions.

Example testing results are described below.
Changes in Acoustic Velocity:

Acoustic measurements can assess compaction induced during loading processes for both compressional ($V_p$) and shear ($V_s$) waves under triaxial confining pressure conditions using a linear variable differential transducer (LVDT). In this example, the measurements were acquired under three confining pressures (21.2, 36.1, and 48.2 MPa) for ten cycles to simulate compaction processes that led to changes in porosity and permeability. The results (shown in FIG. 4) show that a power trend line with $R^2 \approx 1.0$, and the average change compressional velocity ($\Delta V_p$) between loading cycle one and cycle 10 is around 100 ft/sec, indicating compaction was induced.

Pore Size Reduction and Pore Throat Damage:

Pore and pore throat connectivity/damage can be visualized and characterized from high-resolution micro-CT scan images. The characterization of pore geometry provides valuable data for the understanding and modeling of fluid transport and mechanical processes occurring in a real porous media system. Pore size distribution by porosimetry was adopted here, considering the connectivity to the intrusion-sided and closed pores.

Figure 5:
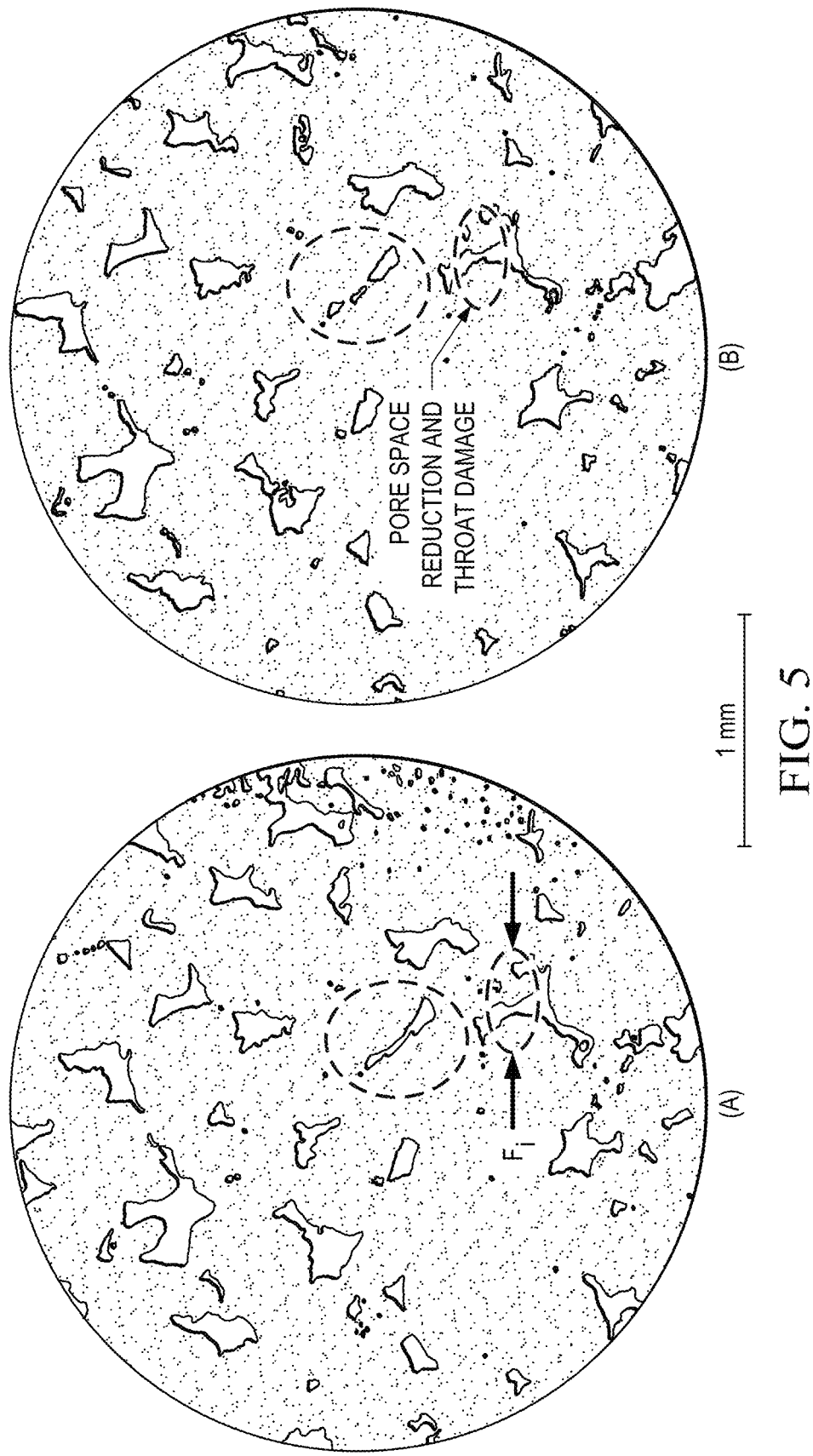
FIGS. 5-7 show, for three respective samples, the pore size distribution and pore throat geometry before applying forces, and the pore size reduction and pore throat damage after loading.
Figure 6:
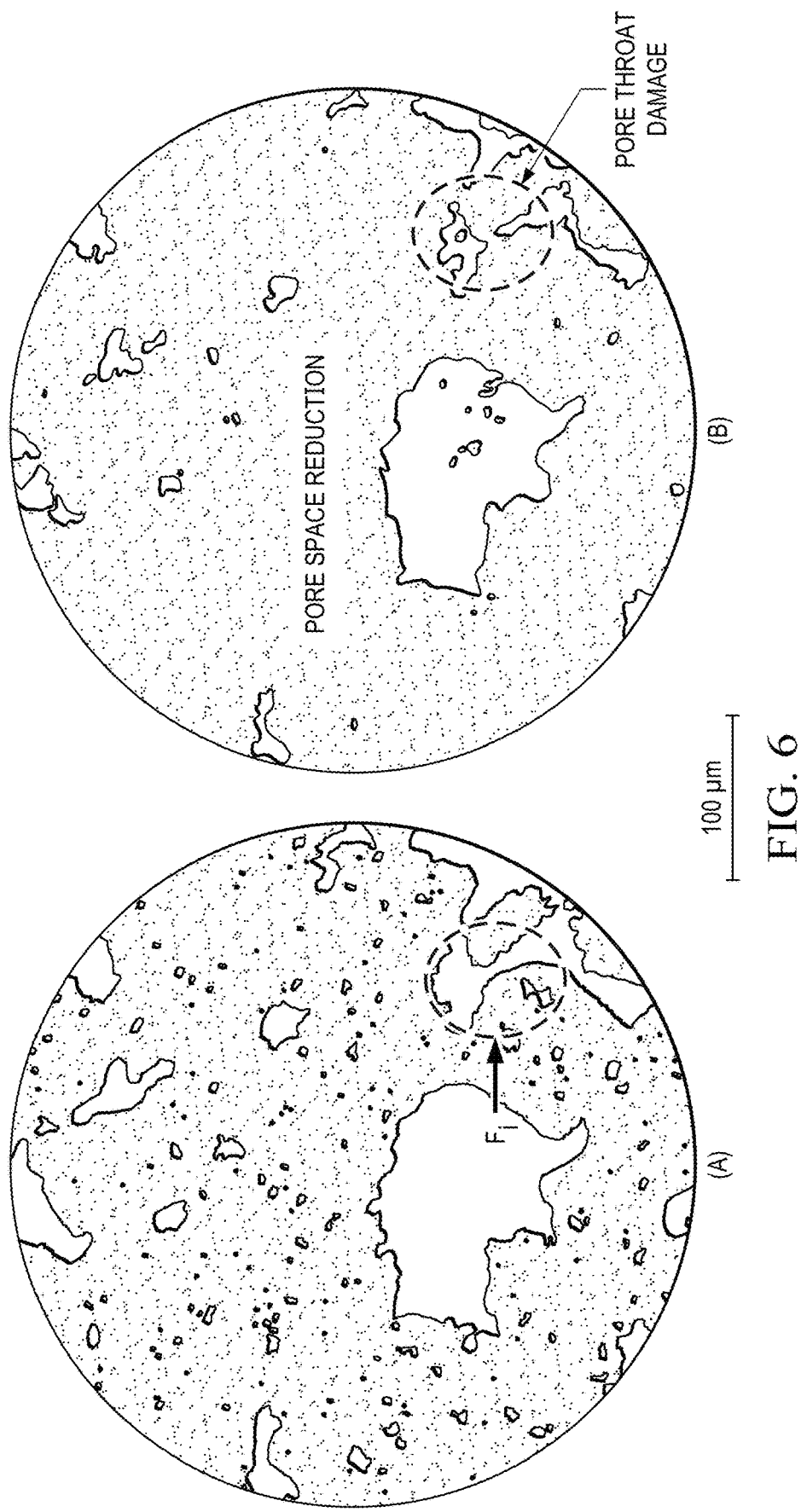
Figure 7:
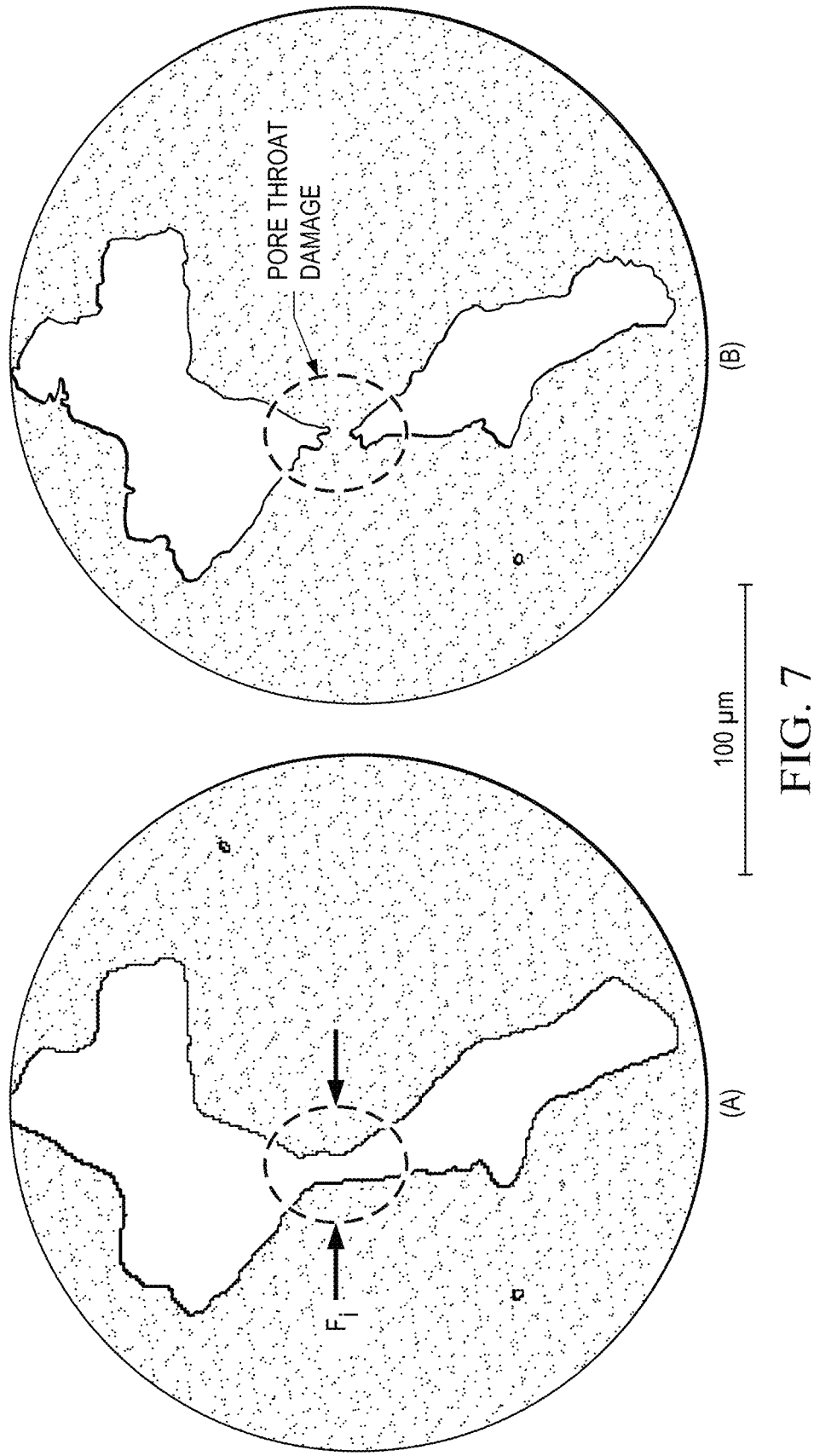

FIGS. 5-7 show, for three respective samples, the pore size distribution, and pore throat geometry before applying forces (panels "a"), the pore size reduction and pore throat damage after loading (panels "b"), and the acting forces direction in scale from 1 mm to 100 μm. In this example, there is an apparent reduction in porosity as micro-pores were reduced. The reduction in permeability can be inferred from the pore throat damage.

Figure 8:
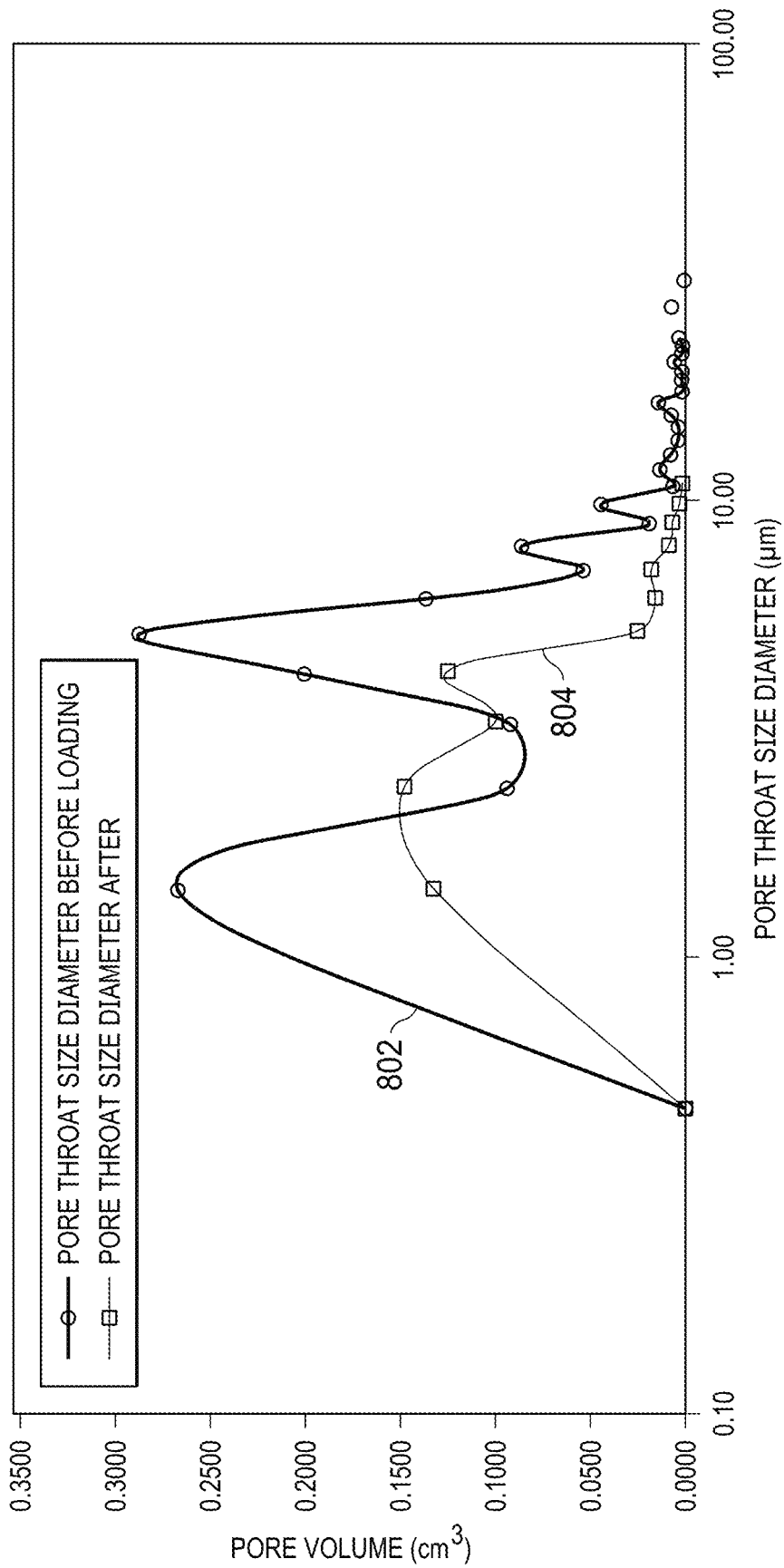
FIG. 8 is a plot showing a comparison between pore throat size diameter and pore volume during loading and unloading cycles.
Figure 9:
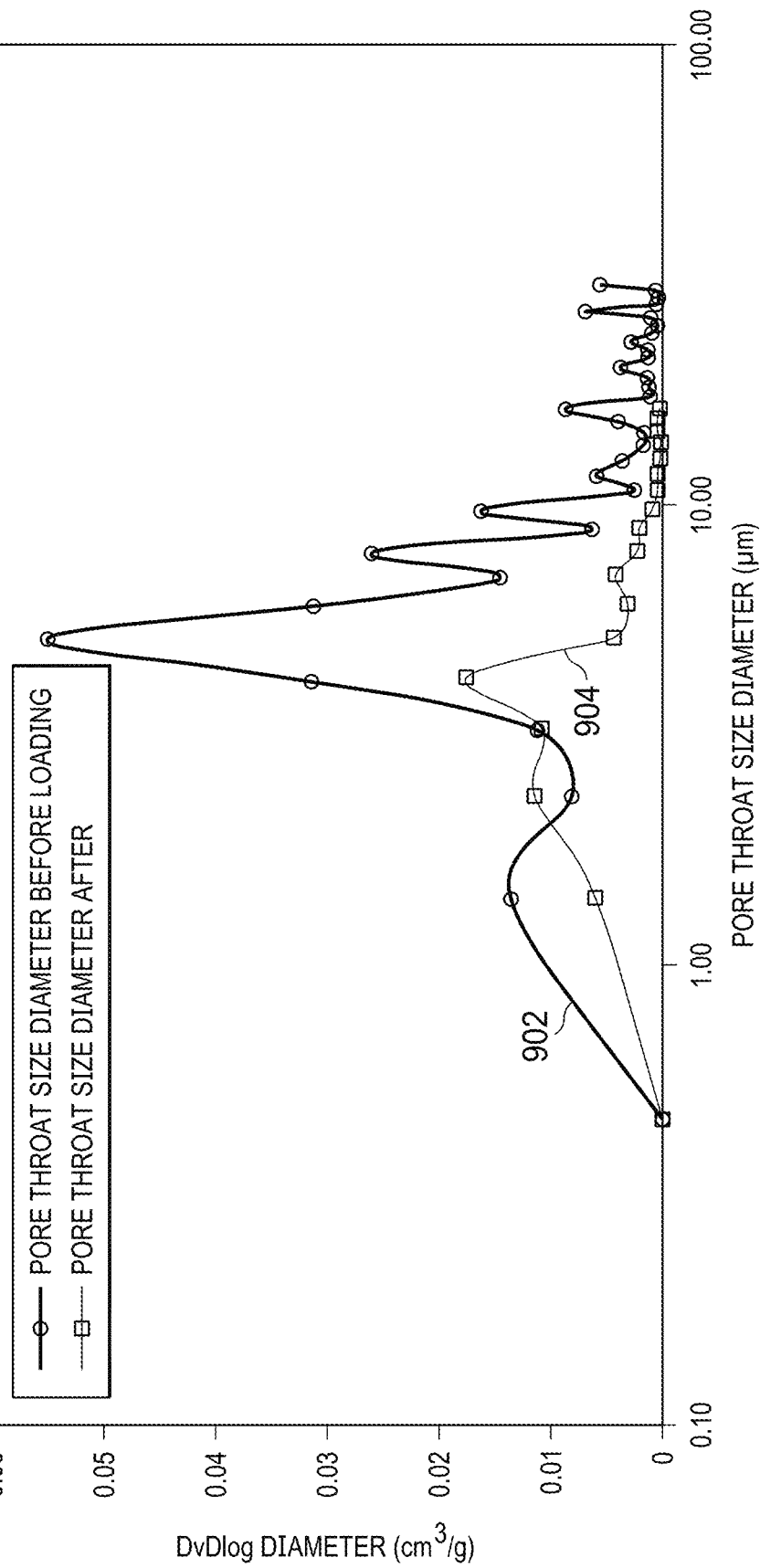
FIG. 9 is a plot showing a comparison between pore throat size diameter, differential pore volume, and differential diameter dV/dR during loading and unloading cycles.

Further, the porosimetry technique was used to determine the pore size and pore throat distribution by the intrusion of a liquid. FIG. 8 shows the characteristics of pore throat diameter versus pore volume before loading (curve 802) and after loading (curve 804). This plot reflects clear damage in the pore throat, as indicated by the reduction in pore volume, the pore throat diameter generally ranging from 0.6 to 10 μm before and after loading Further, FIG. 9 shows the relationship between pore throat and differential pore volume/pore throat diameter dV/dR before loading (curve 902) and after loading (curve 904). This plot indicates that the pore throat damage occurred due to multi-cycles of loading and unloading.

Figure 10:
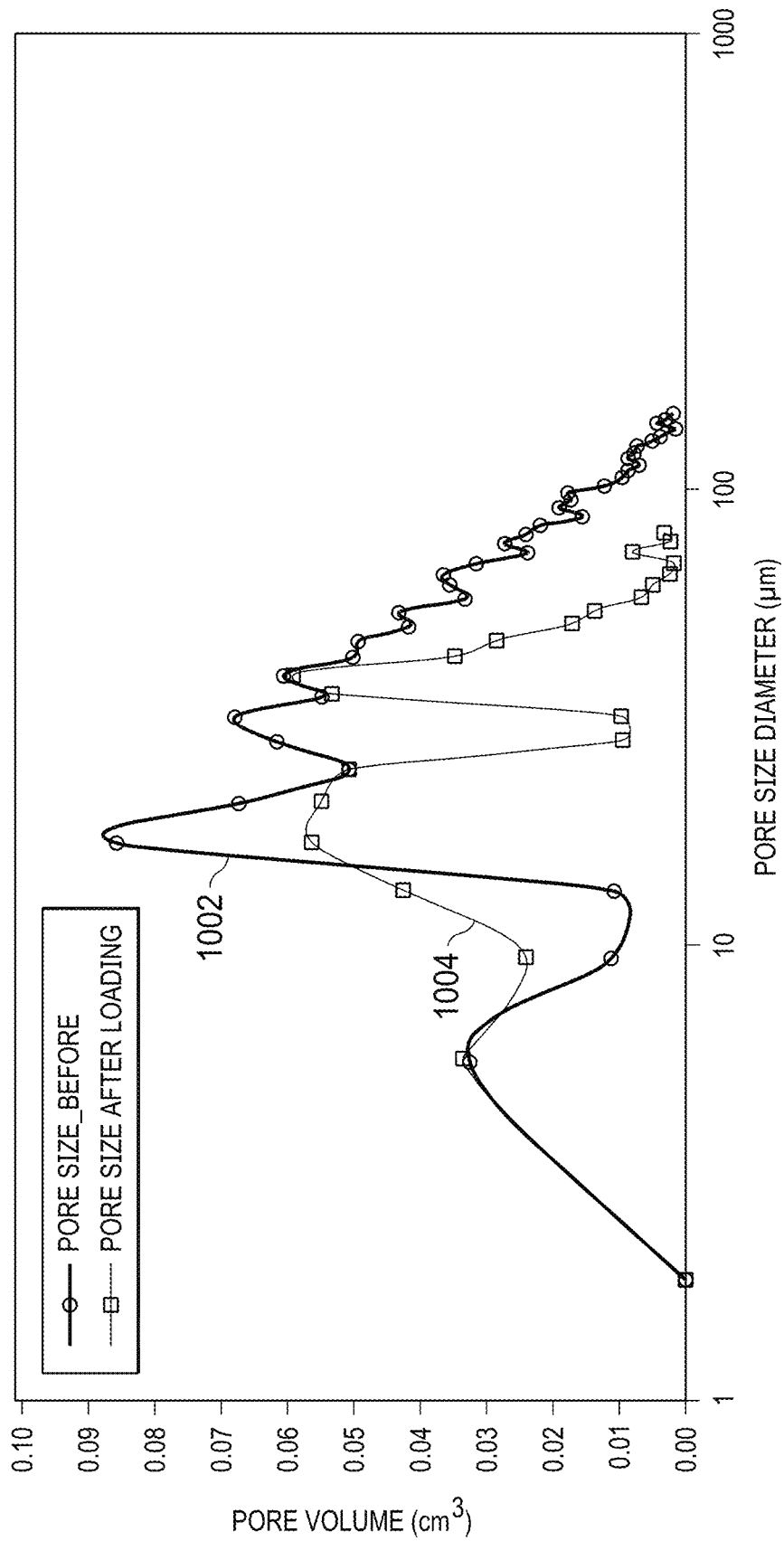
FIG. 10 is a plot showing a comparison between pore size diameter and pore volume during loading and unloading cycles.

FIG. 10 shows characteristics of pore size diameter versus pore volume before loading (curve 1002) and after loading (curve 1004). This plot indicates a clear reduction in the pore diameter, as indicated by reduction in pore volume, the pore diameter generally ranging from 0.3 to 100 μm before and after loading.

Figure 11:
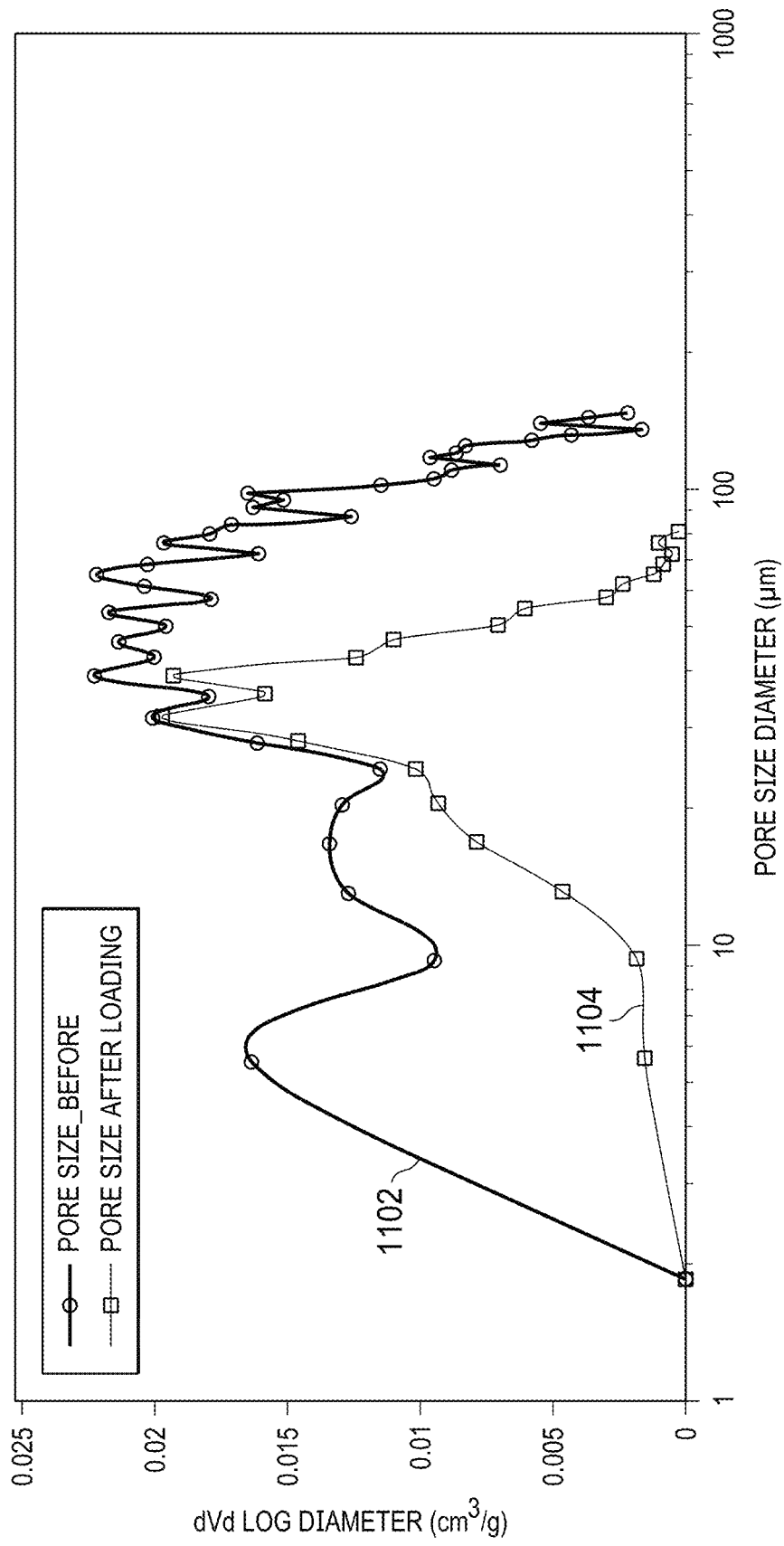
FIG. 11 is a plot showing a comparison between pore size diameter, differential pore volume, and differential diameter dV/dR during loading and unloading cycles.

FIG. 11 shows the relationship between pore size diameter and differential pore volume/pore throat diameter dV/dR before loading (curve 1102) and after loading (curve 1104). This plot indicates that the pore throat damage occurred due to multiple cycles of loading and unloading.

Permeability and Fluid Flow Simulation:

As the reservoir compacts due to pore volume collapse, reservoir permeability also decreases. A simulation of the effective permeability and fluid flow was performed using the modified Stokes-Brinkman solver. In this approach, the simulation was performed for a series of ten cycles of loading and unloading.

Multi-scale digital rock analysis is conceptually well-suited for sandstones analysis and petrophysical modeling, as it allows varying resolution and provides a systematic procedure for coarsening and refinement. Darcy's model is used to approximate pressure and fluxes on a coarse grid in large-scale discontinuities, whereas fine-scale effects are captured through basis functions computed numerically by solving local Stokes-Brinkman flow problems on the underlying fine-scale cellular grid. The Stokes-Brinkman equations provide a unified approach to simulating free-flow and porous regions using a single system of equations. Further, these equations avoid explicit interface modeling and reduce to Darcy or Stokes flow in certain parameter limits. Further, high-resolution CT imaging was performed to build pore structures for the flow analysis.

Numerical modeling of permeability was based on the highest magnification tomography at 0.5 to 3 μm resolution. Three-dimensional images were segmented to allow porosity and permeability computation at sub-sample scales. Two main phases have been identified: pores and grains.

Incompressible flow in a porous rock matrix typically obeys Darcy's Law and is described by a first-order elliptic system in which Darcy's Law is combined with a mass-conservation equation to relate the pressure and the total (interstitial) velocity. Incompressible flow in open domains, on the other hand, obeys the Stokes equations. The Stokes-Brinkman equations combine Darcy and Stokes models into a single equation. This model provides a unified approach to model flow in the intergranular porous subdomains using a single system of equations. In the free-flow (or fluid) domain, it is assumed that permeability tends to infinity and sets the effective viscosity equal to the fluid viscosity. Otherwise, it transforms into the coupled Darcy-Stokes equations, which reintroduces the requirement for interface conditions and computational intractability.

Figure 12:
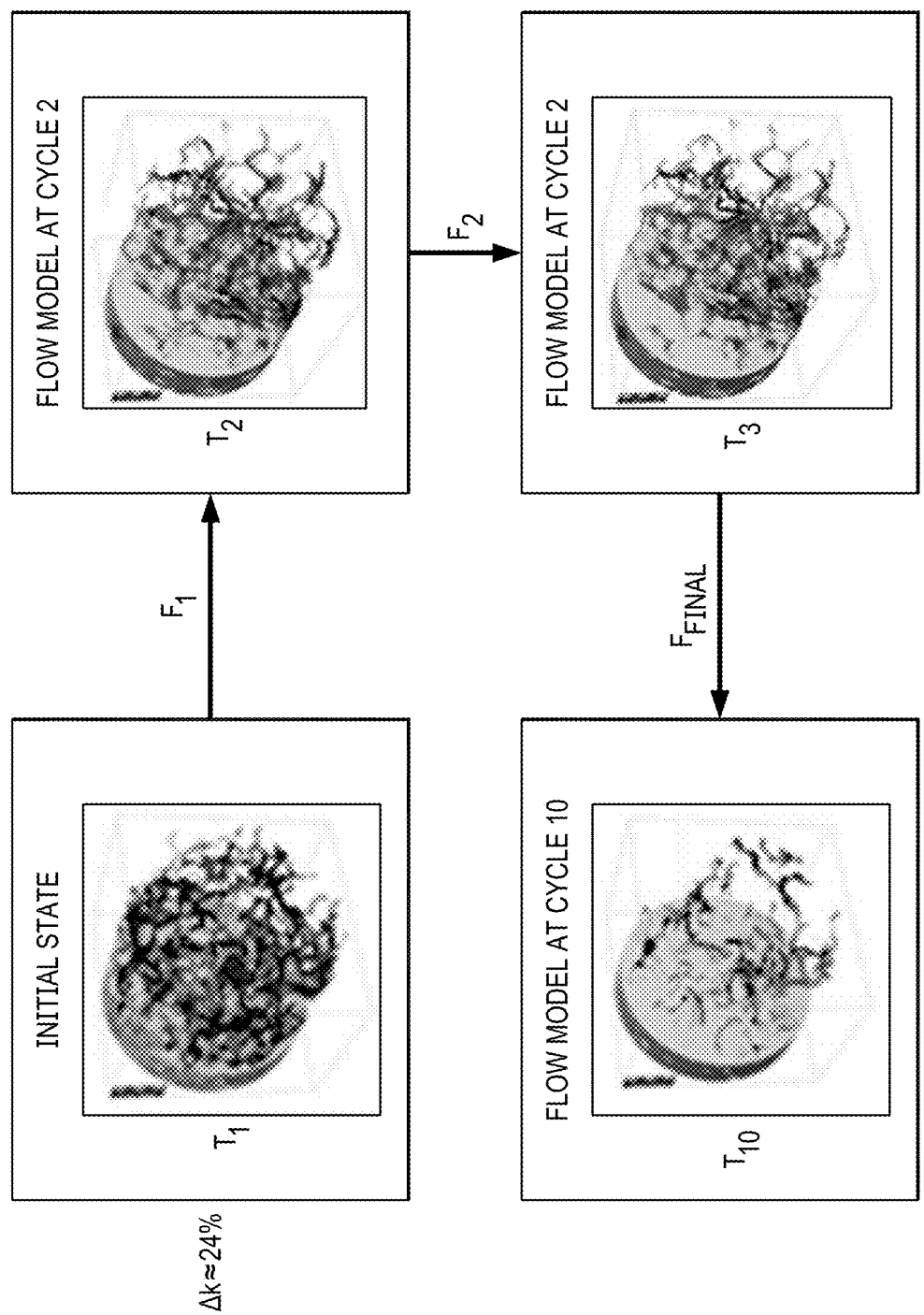
FIG. 12 shows an example of an effective permeability simulation for a series of loading and unloading cycles.

The original structure, porosity segmentation, velocity field, and illuminated streamlines are illustrated in FIG. 12. The porosities are in the range of (8-17) pu before loading and (5-13) pu after ten cycles of loading, whereas the permeability is in the range of (15.25-259.6) mD for the studied samples before loading and (11.4-197.3) mD after ten cycles of loading.

A flow-based upscaling procedure based on the Stokes-Brinkman equation can be used to compute effective permeability on coarser grids. To build a coarser grid, the permeability of the unresolved porous materials can be estimated within the grid. The results of the modeling illustrate permeability degradation in three orthogonal directions. The closure of the pore throats and reduction of pore bodies contributes to the bulk drop of permeability in comparison to the original value of permeability before mechanical testing.

Example Processes

Figure 13:
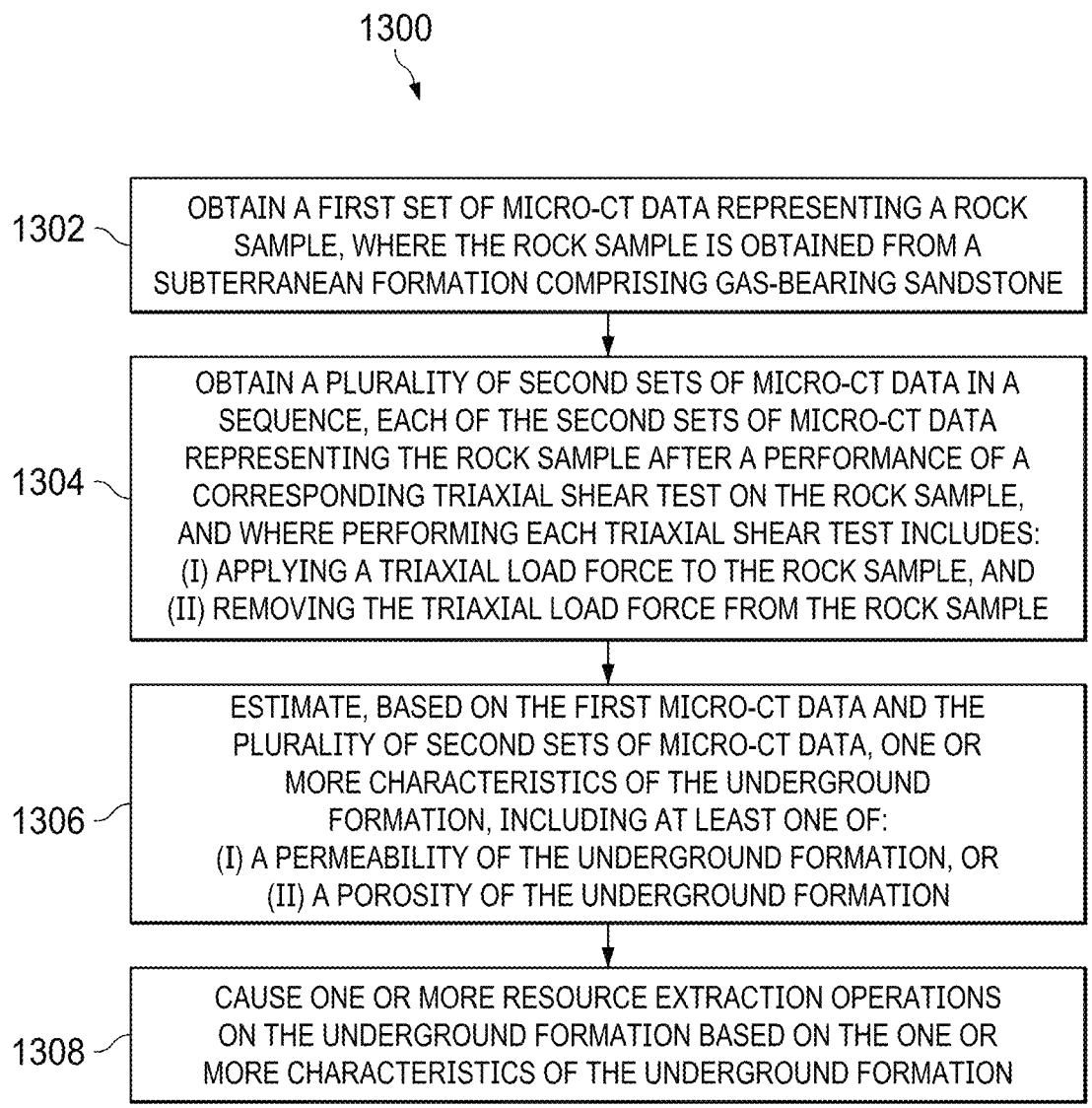
FIG. 13 is a flow chart diagram of an example process for assessing the characteristics of a subterranean formation.

FIG. 13 shows an example process 1300 for assessing the characteristics of a subterranean formation. In some implementations, the process 1300 can be performed by the system 100 described in this disclosure (for example, the system 100 including the rock analysis system 150 shown and described with reference to FIG. 1A) using one or more processors (for example, using the processor or processors 1410 shown in FIG. 14).

In the process 1300, a system obtains a first set of micro-computed tomography (micro-CT) data representing a rock sample (block 1302). The rock sample is obtained from a subterranean formation that includes gas-bearing sandstone.

In some implementations, the rock sample can be a "thick wall cylinder" rock sample. For example, the rock sample can include a cylindrical portion of rock extending along an axis, and an aperture defined through the cylindrical portion and extending along the axis. In some implementations, a diameter of the cylindrical portion can be approximately 3 inches in height and can have an outer diameter of approximately 1.5 inches. Further, the aperture can have a diameter of approximately 0.5 inches.

The system obtains a plurality of second sets of micro-CT data in a sequence (block 1304). Each of the second sets of micro-CT data represents the rock sample after a performance of a corresponding triaxial shear test on the rock sample. Performing each triaxial shear test includes applying a triaxial load force to the rock sample, and removing the triaxial load force from the rock sample.

In some implementations, each of the first micro-CT data and the plurality of second sets of micro-CT data can include one or more images having a voxel size of 3 μm or less along a dimension. For example, at least some of the micro-CT images can be three-dimensional images, within a pixel size of 3 μm×3 μm×3 μm or smaller.

The system estimates, based on the first micro-CT data and the plurality of second sets of micro-CT data, one or more characteristics of the underground formation (block 1306). The one or more characteristics includes a permeability of the underground formation and/or a porosity of the underground formation.

In some implementations, estimating the one or more characteristics of the underground formation can include modeling a fluid of flow through the underground formation.

In some implementations, estimating the one or more characteristics of the underground formation can include modeling an elasticity of the underground formation.

In some implementations, estimating the one or more characteristics of the underground formation can include determining a change in a pore size of the underground formation in response to performance of the triaxial shear tests.

In some implementations, estimating the one or more characteristics of the underground formation can include determining a change in a pore throat size of the underground formation in response to performance of the triaxial shear tests.

In some implementations, estimating the one or more characteristics of the underground formation can include determining a change an acoustic velocity through the underground formation.

The computer system causes one or more resource extraction operations on the underground formation based on the one or more characteristics of the underground formation (block 1308). In some implementations, the one or more resource extraction operations can include regulating an extraction of resources from the underground formation based on the one or more characteristics of the underground formation (for example, as a part of a depletion process). In some implementations, the one or more resource extraction operations can include regulating an injection of a substance into the underground formation based on the one or more characteristics of the underground formation (for example, as a part of an injection process).

Example Systems

Some implementations of the subject matter and operations described in this specification can be implemented in digital electronic circuitry, or in computer software, firmware, or hardware, including the structures, disclosed in this specification and their structural equivalents, or in combinations of one or more of them. For example, in some implementations, one or more components of the system 100 and the rock analysis system 150 can be implemented using digital electronic circuitry, or in computer software, firmware, or hardware, or in combinations of one or more of them. In another example, the process 1300 shown in FIG. 13 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, that is, one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The term "data processing apparatus" encompasses all kinds of apparatus, devices, and machines for processing data, including by way of example programmable processor, a computer, a system on a chip, or multiple ones, or combinations, of the foregoing. The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as special purpose logic circuitry, for example, an FPGA (field programmable gate array) or an ASIC (application specific integrated circuit).

Processors suitable for the execution of a computer program include, by way of example, both general and special purpose microprocessors and processors of any kind of digital computer. Generally, a processor will receive instructions and data from a read only memory or a random access memory, or both. A computer includes a processor for performing actions in accordance with instructions and one or more memory devices for storing instructions and data. A computer can also include or be operatively coupled to receive data from or transfer data to, or both, one or more mass storage devices for storing data, for example, magnetic, magneto-optical disks, or optical disks. However, a computer need not have such devices. Devices suitable for storing computer program instructions and data include all forms of non-volatile memory, media and memory devices, including by way of example semiconductor memory devices (for example, EPROM, EEPROM, AND flash memory devices), magnetic disks (for example, internal hard disks, and removable disks), magneto optical disks, and CD-ROM and DVD-ROM disks. The processor and the memory can be supplemented by, or incorporated in, special purpose logic circuitry.

To provide for interaction with a user, operations can be implemented on a computer having a display device (for example, a monitor or another type of display device) for displaying information to the user. The computer can also include a keyboard and a pointing device (for example, a mouse, a trackball, a tablet, a touch-sensitive screen, or another type of pointing device) by which the user can provide input to the computer. Other kinds of devices can be used to provide for interaction with a user as well. For example, feedback provided to the user can be any form of sensory feedback, such as visual feedback, auditory feedback, or tactile feedback. Input from the user can be received in any form, including acoustic, speech, or tactile input. In addition, a computer can interact with a user by sending documents to and receiving documents from a device that is used by the user. For example, a computer can send web pages to a web browser on a user's client device in response to requests received from the web browser.

A computer system can include a single computing device or multiple computers that operate in proximity or generally remote from each other and typically interact through a communication network. Examples of communication networks include a local area network ("LAN") and a wide area network ("WAN"), an inter-network (for example, the Internet), a network including a satellite link, and peer-to-peer networks (for example, ad hoc peer-to-peer networks). A relationship between client and server can arise by virtue of computer programs running on the respective computers and having a client-server relationship with each other.

Figure 14:
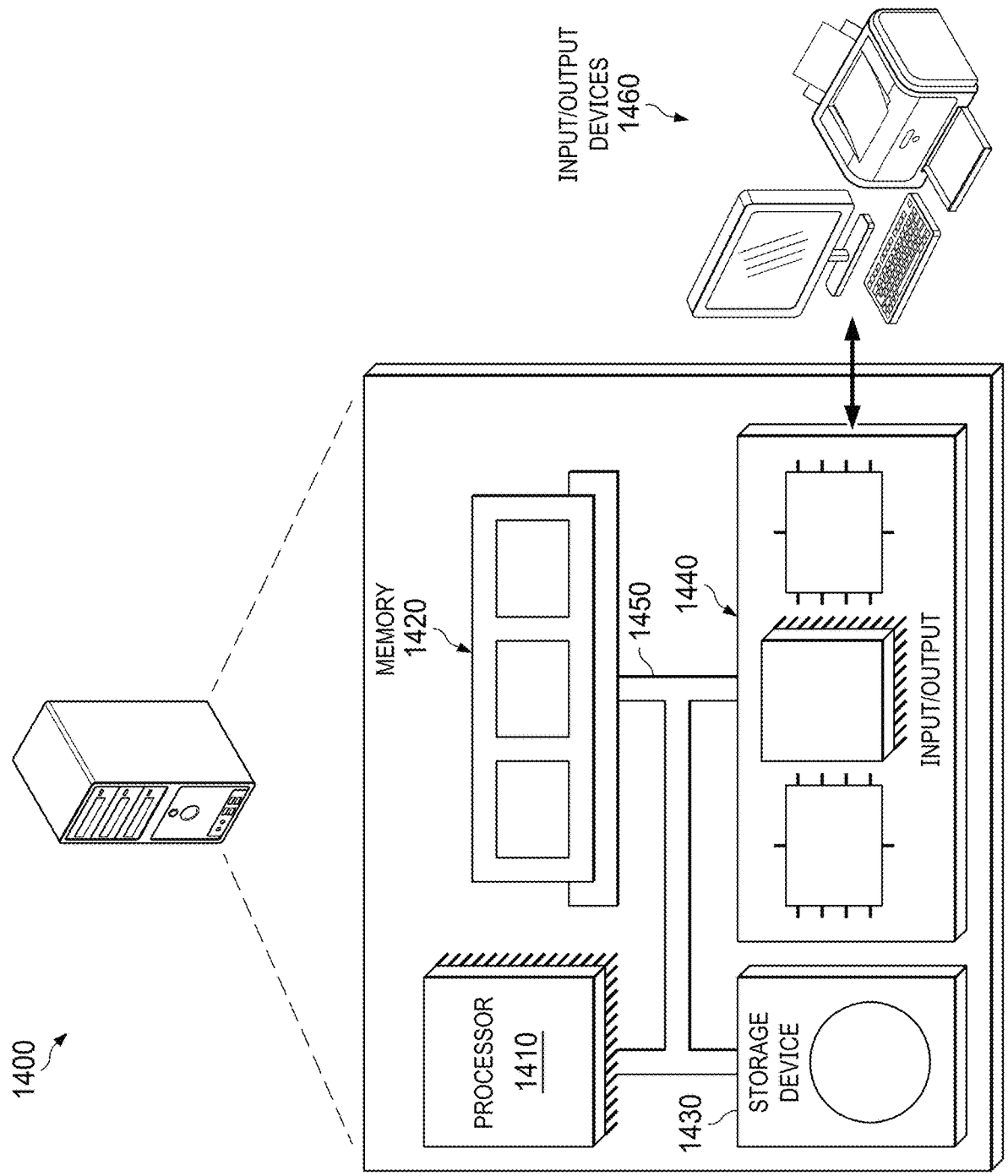
FIG. 14 is a schematic diagram of an example computer system.

FIG. 14 shows an example computer system 1400 that includes a processor 1410, a memory 1420, a storage device 1430, and an input/output device 1440. Each of the components 1410, 1420, 1430 and 1440 can be interconnected, for example, by a system bus 1450. The processor 1410 is capable of processing instructions for execution within the system 1400. In some implementations, the processor 1410 is a single-threaded processor, a multi-threaded processor, or another processor type. The processor 1410 is capable of processing instructions stored in the memory 1420 or on the storage device 1430. The memory 1420 and the storage device 1430 can store information within the system 1400.

The input/output device 1440 provides input/output operations for the system 1400. In some implementations, the input/output device 1440 can include one or more of a network interface device, for example, an Ethernet card, a serial communication device, for example, an RS-232 port, or a wireless interface device, for example, an 802.11 card, a 3G wireless modem, a 4G wireless modem, or a 5G wireless modem, or both. In some implementations, the input/output device can include driver devices configured to receive input data and send output data to other input/output devices, for example, keyboard, printer, and display devices 1460. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, various modifications can be made without departing from the spirit and scope of the invention. Accordingly, other embodiments are within the scope of the claims.

What is claimed is:

1. A method comprising:
   obtaining, by a computer system, a first set of micro-computed tomography (micro-CT) data representing a rock sample, wherein the rock sample is obtained from an underground formation comprising gas-bearing sandstone;
   obtaining by the computer system, a plurality of second sets of micro-CT data in a sequence, wherein each of the second sets of micro-CT data represents the rock sample after a performance of a corresponding triaxial shear test on the rock sample, and wherein performing each triaxial shear test comprises:
      applying a triaxial load force to the rock sample, and
      removing the triaxial load force from the rock sample;
   estimating, by the computer system based on the first micro-CT data and the plurality of second sets of micro-CT data, one or more characteristics of the underground formation, wherein the one or more characteristics comprises at least one of:
      a permeability of the underground formation, or
      a porosity of the underground formation; and
   causing, by the computer system, one or more resource extraction operations to be performed on the underground formation based on the one or more characteristics of the underground formation.

2. The method of claim 1, wherein the rock sample comprises:
   a cylindrical portion of rock extending along an axis, and
   an aperture defined through the cylindrical portion and extending along the axis.

3. The method of claim 2, wherein a diameter of the cylindrical portion is approximately 3 inches in height and has an outer diameter of approximately 1.5 inches, and
   wherein the aperture has a diameter of approximately 0.5 inches.

4. The method of claim 1, wherein each of the first micro-CT data and the plurality of second sets of micro-CT data comprise:
   one or more images having a voxel size of 3 μm or less along a dimension.

5. The method of claim 1, wherein estimating the one or more characteristics of the underground formation comprises:
   modeling a fluid of flow through the underground formation.

6. The method of claim 1, wherein estimating the one or more characteristics of the underground formation comprises:
   modeling an elasticity of the underground formation.

7. The method of claim 1, wherein estimating the one or more characteristics of the underground formation comprises:
   determining a change in a pore size of the underground formation in response to performance of the triaxial shear tests.

8. The method of claim 1, wherein estimating the one or more characteristics of the underground formation comprises:
   determining a change in a pore throat size of the underground formation in response to performance of the triaxial shear tests.

9. The method of claim 1, wherein estimating the one or more characteristics of the underground formation comprises:
   determining a change in an acoustic velocity through the underground formation.

10. The method of claim 1, wherein the one or more resource extraction operations comprises:
    regulating an extraction of resources from the underground formation based on the one or more characteristics of the underground formation.

11. The method of claim 1, wherein the one or more resource extraction operations comprises:
    regulating an injection of a substance into the underground formation based on the one or more characteristics of the underground formation.

12. A system comprising:
    one or more processors; and
    one or more non-transitory computer readable media storing instructions that, when executed by the one or more processors, cause the one or more processors to perform operations comprising:
       obtaining a first set of micro-computed tomography (micro-CT) data representing a rock sample, wherein the rock sample is obtained from an underground formation comprising gas-bearing sandstone;

obtaining a plurality of second sets of micro-CT data in a sequence, wherein each of the second sets of micro-CT data represents the rock sample after a performance of a corresponding triaxial shear test on the rock sample, and wherein performing each triaxial shear test comprises:
   applying a triaxial load force to the rock sample, and removing the triaxial load force from the rock sample;
estimating, based on the first micro-CT data and the plurality of second sets of micro-CT data, one or more characteristics of the underground formation, wherein the one or more characteristics comprises at least one of:
   a permeability of the underground formation, or
   a porosity of the underground formation; and
causing one or more resource extraction operations to be performed on the underground formation based on the one or more characteristics of the underground formation.

13. One or more non-transitory computer readable media storing instructions that, when executed by one or more processors, cause the one or more processors to perform operations comprising:

obtaining a first set of micro-computed tomography (micro-CT) data representing a rock sample, wherein the rock sample is obtained from an underground formation comprising gas-bearing sandstone;
obtaining a plurality of second sets of micro-CT data in a sequence, wherein each of the second sets of micro-CT data represents the rock sample after a performance of a corresponding triaxial shear test on the rock sample, and wherein performing each triaxial shear test comprises:
   applying a triaxial load force to the rock sample, and removing the triaxial load force from the rock sample;
estimating, based on the first micro-CT data and the plurality of second sets of micro-CT data, one or more characteristics of the underground formation, wherein the one or more characteristics comprises at least one of:
   a permeability of the underground formation, or
   a porosity of the underground formation; and
causing one or more resource extraction operations to be performed on the underground formation based on the one or more characteristics of the underground formation.

* * * * *